US010646141B2

(12) United States Patent
Liu (10) Patent No.: US 10,646,141 B2
(45) Date of Patent: May 12, 2020

(54) METHOD AND DEVICE FOR DETERMINING HEAD MOVEMENT (71) Applicant: Beijing Zhigu Rui Tuo Tech Co., Ltd, Beijing (CN)

(72) Inventor: Hao Liu, Beijing (CN)

(73) Assignee: Beijing Zhigu Rui Tuo Tech Co., Ltd, Beijing (CN)

(*) Notice: Subject to any disclaimer, the term of this patent is extended or adjusted under 35 U.S.C. 154(b) by 183 days.

(21) Appl. No.: 15/570,310

(22) PCT Filed: Apr. 29, 2016

(86) PCT No.: PCT/CN2016/080600
§ 371 (c)(1),
(2) Date: Oct. 27, 2017

(87) PCT Pub. No.: WO2016/173522
PCT Pub. Date: Nov. 3, 2016

(65) Prior Publication Data
US 2018/0132763 A1 May 17, 2018

(30) Foreign Application Priority Data
Apr. 30, 2015 (CN) .......................... 2015 1 0219954

(51) Int. Cl.
A61B 5/11 (2006.01)
A61B 5/0488 (2006.01)
(Continued)

(52) U.S. Cl.
CPC ........ A61B 5/1126 (2013.01); A61B 5/04012 (2013.01); A61B 5/0488 (2013.01);
(Continued)

(58) Field of Classification Search
CPC . A61B 5/1126; A61B 5/1114; A61B 5/04012; A61B 5/0488; A61B 5/6803;
(Continued)

(56) References Cited

U.S. PATENT DOCUMENTS 8,223,024 B1 * 7/2012 Petrou .................. G02B 27/017
340/573.1
2007/0010748 A1 1/2007 Rauch et al.
(Continued)

FOREIGN PATENT DOCUMENTS

CN 1767873 A 5/2006
CN CN101711709 A 5/2010
(Continued)

OTHER PUBLICATIONS

Chinese Office Action dated Jun. 29, 2018 for Chinese Application No. 201510219954.6, 18 pages (with translation).
(Continued)

Primary Examiner — Eric F Winakur
Assistant Examiner — Abid A Mustansir
(74) Attorney, Agent, or Firm — Amin, Turocy & Watson, LLP (57) ABSTRACT Electronic devices are provided that can determine a head movement. A method comprises: acquiring, in response to a head movement performed by a user, myoelectricity information of an eye of the user; and determining information related to the head movement according to the myoelectricity information and at least one piece of reference information. A head movement can be identified according to the myoelectricity information, which helps improve accuracy of head movement identification.

22 Claims, 5 Drawing Sheets (51) Int. Cl.
  *A61B 5/0496* (2006.01)
  *A61B 5/00* (2006.01)
  *G06F 3/01* (2006.01)
  *A61B 5/04* (2006.01)

(52) U.S. Cl.
  CPC .......... *A61B 5/0496* (2013.01); *A61B 5/1114* (2013.01); *A61B 5/1121* (2013.01); *A61B 5/1123* (2013.01); *A61B 5/6803* (2013.01); *G06F 3/012* (2013.01); *G06F 3/015* (2013.01)

(58) Field of Classification Search
  CPC ... A61B 5/1123; A61B 5/1121; A61B 5/0496; G06F 3/015; G06F 3/012
  See application file for complete search history.

(56) References Cited

U.S. PATENT DOCUMENTS

| | | | | |
|---|---|---|---|---|
| 2009/0105817 | A1* | 4/2009 | Bretthauer | A61B 3/113 623/4.1 |
| 2012/0265080 | A1* | 10/2012 | Yu | A61B 5/04 600/484 |
| 2018/0136465 | A1* | 5/2018 | Chi | G02B 27/017 |

FOREIGN PATENT DOCUMENTS

| CN | 202096374 U | 1/2012 |
|---|---|---|
| CN | CN102968072 A | 3/2013 |
| CN | 104199546 A | 12/2014 |
| CN | CN104503592 A | 4/2015 |
| CN | CN104503593 A | 4/2015 |

OTHER PUBLICATIONS

International Search Report for PCT Application No. PCT/CN2016/080600, dated Aug. 4, 2016, 3 pages.

Xu, Zhang, et al., "Exploration on the Feasibility of Building Muscle-Computer Interfaces using Neck and Shoulder Motions", 31st Annual International Conference of the IEEE EMBS Minneapolis, Minnesota, USA, Sep. 2-6, 2009, pp. 7018-7021.

* cited by examiner

Submodule for determining the
number of times 522

Target waveform determining unit
5221a

Unit for determining the number of
times 5222a

FIG. 10

Submodule for determining the
number of times 522

Target signal characteristic
determining unit 5221b

Unit for determining the number of
times 5222b

METHOD AND DEVICE FOR DETERMINING HEAD MOVEMENT

RELATED APPLICATION

The present application is a U.S. National Stage filing under 35 U.S.C. § 371 of international patent cooperation treaty (PCT) application No. PCT/CN2016/080600, filed Apr. 29, 2016, and entitled "METHOD AND DEVICE FOR DETERMINING HEAD MOVEMENT", which claims the benefit of priority to Chinese Patent Application No. 201510219954.6, filed on Apr. 30, 2015, which applications are hereby incorporated into the present application by reference herein in their respective entireties.

TECHNICAL FIELD

The present application relates to the field of electronic devices, and, for example, to a method and device for determining a head movement.

BACKGROUND

Currently, new technologies such as wearable computing, mobile computing, and pervasive computing develop rapidly, which put forward new challenges and higher requirements for the human computer interaction technology and provide many new opportunities. In this phase, the nature and harmony human computer interaction manner gets a certain development, and the main characteristic thereof is an multi-channel interaction based on input means such as postures, voice, handwriting, tracking, and expressions, and the objective thereof is to make people perform an interaction operation in a nature way such as using an action, voice, and an expression, which is exactly "user freedom" emphasized by ideal human computer interaction.

In the traditional method for identifying a head movement, a myoelectricity sensor is disposed on the neck of a user, and when the user wants to turn the head, the neck muscles thereof drive the head of the user perform the head turning movement, and at this time, a corresponding myoelectricity signal may be detected, and based on the myoelectricity signal, the head movement of the user may be identified.

By using the foregoing method for identifying a head movement, a maximum amplitude of the detected myoelectricity signal is about 0.5 mV, which results in relatively poor identification accuracy.

SUMMARY

An example objective of the present application is to provide a method and device for determining a head movement, so as to improve identification accuracy.

According to one aspect of at least one example embodiment of the present application, a method for determining a head movement is provided. The method comprises:

acquiring, in response to a head movement performed by a user, myoelectricity information of an eye of the user; and determining information related to the head movement according to the myoelectricity information and at least one piece of reference information.

According to one aspect of at least one embodiment of the present application, a device for determining a head movement is provided. The device comprises:

an acquiring module, configured to acquire, in response to a head movement performed by a user, myoelectricity information of an eye of the user; and a determining module, configured to determine information related to the head movement according to the myoelectricity information and at least one piece of reference information.

In methods and devices according to example embodiments of the present application, in response to a head movement performed by a user, myoelectricity information of an eye of the user is acquired; and according to the myoelectricity information and at least one piece of reference information, information related to the head movement is determined. Therefore, a method for identifying a head movement according to eye myoelectricity information is provided, and a maximum amplitude of the myoelectricity information thereof is higher than 2 mV, and thereby improving identification accuracy; For some devices integrated with myoelectricity sensors, such as a pair of glasses, the method may be used to reuse the myoelectricity information collected by the myoelectricity sensor, and thereby reducing implementation costs.

DETAILED DESCRIPTION

Example embodiments of the present application are further described in detail below with reference to the accompanying drawings and embodiments. The following embodiments are intended to describe the present application, but not to limit the scope of the present application.

A person skilled in the art understands that, in the example embodiments of the present application, the value of the serial number of each step does not mean an execution sequence, and the execution sequence of each step should be determined according to the function and internal logic thereof, and should not be any limitation to the implementation procedure of the example embodiments of the present application.

Figure 1:
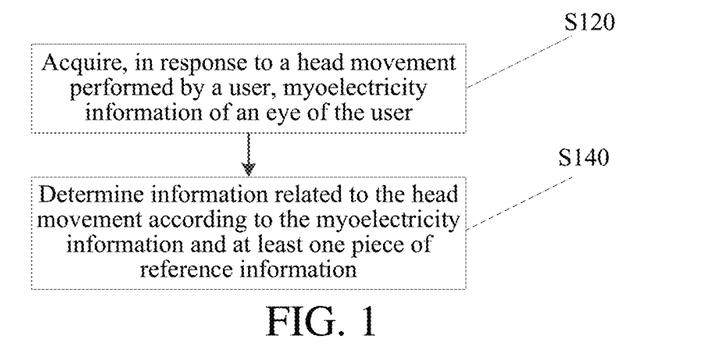
FIG. 1 is a flowchart of a method for determining a head movement according to an example embodiment of the present application.

FIG. 1 is a flowchart of a method for determining a head movement according to an embodiment of the present application. The method may be implemented, for example, on a device for determining a head movement. As shown in FIG. 1, the method comprises:

S120: acquire, in response to a head movement performed by a user, myoelectricity information of an eye of the user; and S140: determine information related to the head movement according to the myoelectricity information and at least one piece of reference information.

In the method according to the embodiment of the present application, in response to a head movement performed by a user, myoelectricity information of an eye of the user is acquired; and according to the myoelectricity information and at least one piece of reference information, information related to the head movement is determined. Therefore, a method for identifying a head movement according to myoelectricity information is provided. A highest value of an amplitude of the myoelectricity information collected by using the method may reach 2 mV, which helps improve accuracy of head movement identification.

The following describes functions of the steps S120 and S140 in detail with reference to the example embodiments.

S120: acquire, in response to a head movement performed by a user, myoelectricity information of an eye of the user.

The head movement refers to a movement performed by the head of the user, for example, head nodding and head shaking. The myoelectricity information may be myoelectricity information of the left eye or myoelectricity information of the right eye of the user. Taking myoelectricity information of the left eye for example, the myoelectricity information of the left eye may be collected on orbicularis oculi muscle of the left eye. The orbicularis oculi muscle is circular muscle around an eye ball in eyelid tissue, and voluntarily and involuntarily powerful contractions of the orbicularis oculi muscle make people voluntarily and involuntarily eye blinking. Specifically, for example, the myoelectricity information may be acquired by using a myoelectricity sensor on a pair of smart glasses.

Figure 2:
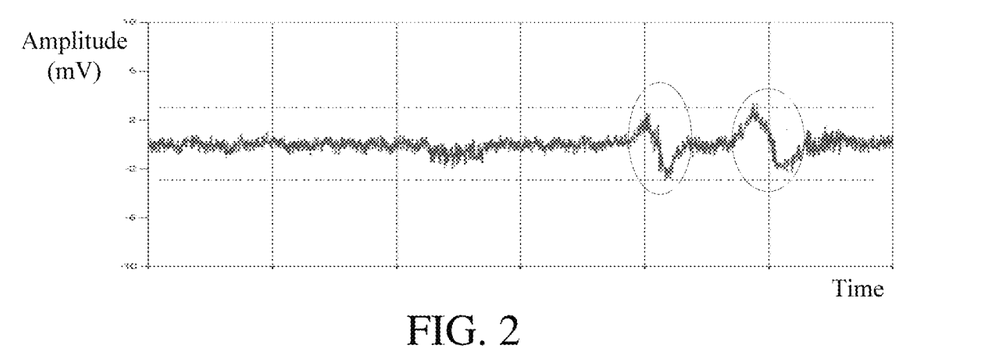
FIG. 2 is a schematic waveform diagram of eye myoelectricity information corresponding to a head shaking movement according to an example embodiment of the present application.

FIG. 2 is a waveform diagram of eye myoelectricity information collected in response to a head shaking movement performed by a user, wherein waveforms in ellipses are myoelectricity waveforms corresponding to the head shaking movement of the user, and waveforms outside the ellipses are myoelectricity waveforms when the user does not perform any head movement. It can be seen that when the user performs the head shaking movement, an amplitude of eye myoelectricity may significantly increase, and a maximum amplitude thereof may exceed 2 mV.

During the research process, the inventor finds that, an eye myoelectricity signal, for example, main energy of a myoelectricity signal of the orbicularis oculi muscle is concentrated within a range of 50 Hz to 150 Hz, and an average amplitude is about 0.5 mV. When the user performs a head movement such as head nodding, under the influence of a relative movement between a myoelectricity collection electrode and skin and other face or eye muscular movements, the myoelectricity signal of the orbicularis oculi muscle introduces a 0 Hz to 5 Hz eye myoelectricity signal with an obvious waveform, and an average amplitude is about 1.5 mV, and a maximum amplitude exceeds 2 mV. That is to say, the amplitude of the eye myoelectricity caused by the head movement is obviously larger than an amplitude of neck myoelectricity caused by the head movement. Therefore, the present invention uses the eye myoelectricity signal to identify the head movement of the user.

Figure 3:
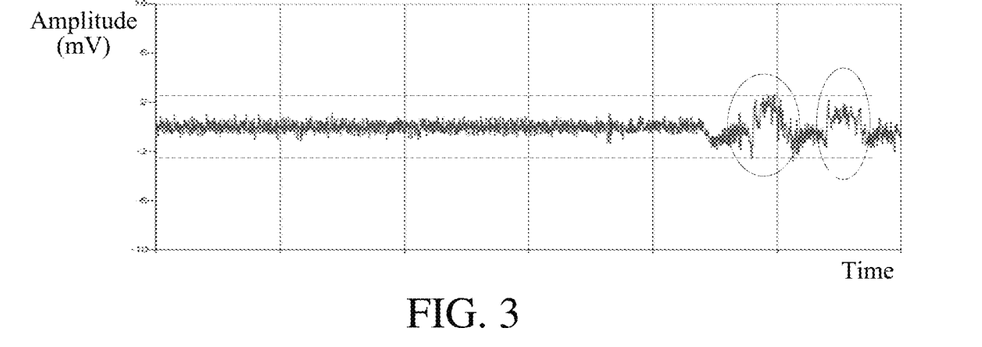
FIG. 3 is a schematic waveform diagram of eye myoelectricity information corresponding to a head nodding movement according to an example embodiment of the present application.

In addition, the inventor further finds that when the user performs different head movements, the obtained waveforms of the eye myoelectricity information have a significant difference. FIG. 3 is a waveform diagram of eye myoelectricity information collected in response to a head nodding movement performed by a user, wherein waveforms in ellipses are myoelectricity waveforms corresponding to a head nodding movement of the user, and waveforms outside the ellipses are myoelectricity waveforms when the user does not perform any head movement. It can be seen that when the user performs the head nodding movement, a maximum amplitude of eye myoelectricity may exceed 2 mV. Meanwhile, it can be seen that the waveforms in the ellipses in FIG. 3 are significantly different from the waveforms in the ellipses in FIG. 2. For example, the change trend of the waveforms in the ellipses in FIG. 2 is first ascending and then descending, and the change trend of the waveforms in the ellipses in FIG. 3 is first descending and then ascending.

Similarity, when the user performs other head movements, corresponding other waveforms of eye myoelectricity may also be obtained. Therefore, identification of different movements may be implemented based on collected eye myoelectricity information, and in addition, an amplitude of eye myoelectricity information triggered by a head movement is obviously higher than an amplitude of myoelectricity information of another part, so that identification accuracy may be improved by identifying the head movement by using the eye myoelectricity information.

S140: Determine information related to the head movement according to the myoelectricity information and at least one piece of reference information.

The information related to the head movement may comprise type of the head movement, for example, head nodding and head shaking. Correspondingly, the step S140 may comprise:

S141: determine the type of the head movement according to the myoelectricity information and the at least one piece of reference information.

In an example embodiment, the step S141 may comprise:

S1411a: determine a target waveform in the myoelectricity information; and

S1412a: determine the type of the head movement according to the target waveform and at least one reference waveform.

In the step S1411a, the target waveform is a waveform corresponding to the head movement in waveforms of the myoelectricity information, which is significantly different from waveforms of myoelectricity information collected when the head does not perform any movement.

Using an example in which the type of the head movement is head shaking movement for example, the obtained waveforms of the myoelectricity information are shown in FIG. 2. The waveforms in the ellipses are waveforms when the head of the user performs the head shaking movement, and the waveforms outside the ellipses are waveforms when the head of the user does not perform any movement. It can be seen that in FIG. 2, the waveforms in the ellipses are significantly different from the waveforms outside the ellipses. Specifically, amplitudes of the waveforms in the ellipses are obviously larger than amplitudes of the waveforms outside the ellipses. Based on this, the target waveforms can be extracted from the myoelectricity information, that is, the waveforms in the ellipses are determined as the target waveforms.

Similarity, FIG. 3 shows waveforms of the myoelectricity information obtained when the type of the head movement is head nodding. The waveforms in the ellipses are waveforms when the head of the user performs the head nodding movement, and the waveforms outside the ellipses are waveforms when the head of the user does not perform any movement. It can be seen that in FIG. 3, amplitudes of the waveforms in the ellipses are also obviously larger than amplitudes of the waveforms outside the ellipses. Based on this, it can be determined that the waveforms in the ellipses are the target waveforms.

In the step S1412a, the reference waveform may be a waveform that corresponds to a corresponding head movement obtained through pre-training, for example, during the training phase, the user may be trained to perform head movements of different types and the corresponding waveforms are correspondingly acquired as the reference waveforms. For example, during the training phase, the user is trained to perform a head nodding movement, and a waveform in the ellipse in FIG. 3 is correspondingly acquired as a reference waveform corresponding to the head nodding movement.

When the number of the at least one reference waveform is relatively smaller, that is, when there are relatively fewer types of the head movements, whether the target waveform comprises the at least one reference waveform can be determined in an image recognition manner, and if yes, it is determined that the type of the head movement is a type corresponding to the comprised reference waveform. Taking FIG. 2 and FIG. 3 for example, it can be seen that the target waveforms in FIG. 2 are significantly different from the target waveforms in FIG. 3. For example, the trend of the target waveforms in FIG. 2 is first ascending and then descending, and the trend of the target waveforms in FIG. 3 is first descending and then ascending. Based on the foregoing difference, it can be determined that the target waveforms correspond to different reference waveforms, that is, the target waveforms are identified.

When the number of the at least one reference waveform is relatively large, a probability of confusing different reference waveforms is increasing. In order to avoid an identification error, in an example embodiment, the step S1412a may comprise:

S1412a': calculate cross correlations between the target waveform and the at least one reference waveform respectively, and determine the type of the head movement according to a calculation result.

Specifically, cross correlations between the target waveform and the at least one reference waveform respectively may be calculated to obtain calculation results corresponding to each reference waveform, and then the type corresponding to the reference waveform whose value of the calculation result is the highest (that is, reference waveform that has the highest degree of correlation with the target waveform) may be selected as the type of the head movement. For example, assume that the at least one reference waveform comprises a first reference waveform corresponding to head nodding and a second reference waveform corresponding to head shaking, a cross correlation between the first reference waveform and the target waveform is calculated to obtain a first result, and a cross correlation between the second reference waveform and the target waveform is calculated to obtain a second result, and if the value of the first result is higher than the value of the second result, it can be determined that the type of the head movement is head nodding.

In another example embodiment, the step S141 may comprise:

S1411b: determine a target signal characteristic in the myoelectricity information; and S1412b: determine the type of the head movement according to the target signal characteristic and at least one reference signal characteristic.

In the step S1411b, the target signal characteristic may be understood as a signal characteristic of the target waveform in the foregoing example embodiment, which is correlated with at least one of an amplitude, a phase, and a spectrum of the target waveform. Specifically, the target signal characteristic may comprise at least one of a fingerprint, an average value, and a difference; the fingerprint may be composed of at least one of the amplitude, phase, and spectrum of the target waveform; the average value may be an average value of at least one of the amplitude, phase, and spectrum of the target waveform; and the difference may be a difference of at least one of the amplitude, phase, and spectrum of the target waveform. Certainly, a person skilled in the art understands that, the target signal characteristic may be directly determined according to data of the myoelectricity information, and does not have to be determined according to the target waveform.

In the step S1412b, the reference signal characteristic may be a signal characteristic that corresponds to a corresponding head movement obtained through pre-training, for example, during the training phase, the user may be trained to perform head movements of different types and the signal characteristics of the corresponding myoelectricity information are correspondingly acquired as the reference signal characteristics. For example, during the training phase, the user is trained to perform a head shaking movement, and a signal characteristic of the waveform in the ellipse in FIG. 2 is correspondingly acquired as a reference signal characteristic corresponding to the head shaking movement.

In the step S1412b, whether the target signal characteristic comprises the at least one reference signal characteristic can be determined in a signal characteristic comparison manner, and if yes, it is determined that the type of the head movement is a type corresponding to the comprised reference signal characteristic.

The type of the head movement may indicate different operating commands, for example, head nodding indicates confirmation and head shaking indicates cancellation. Meanwhile, for head movements of different types, different numbers of execution times may also indicate different operating commands, for example, a single head nodding indicates selected and two continuous head noddings indicate open. Therefore, in an example embodiment, the head movement comprises a first type head movement; and the at least one piece of reference information comprises first reference information corresponding to the first type head movement.

Correspondingly, the step S140 may further comprise:

S142: determine the number of times of the first type head movement according to the myoelectricity information and the first reference information.

In an example embodiment, the step S142 may comprise:

S1421a: determine the target waveform in the myoelectricity information; and

S1422a: determine the number of times of the first type head movement according to the number of first reference waveforms comprised in the target waveform.

The implementation principle of the step S1421a is the same as that of the step S1411a, and no further details are provided herein again.

In the step S1422a, the number of the first reference waveforms comprised in the target waveform is corresponding to the number of times of the first type head movement. Assume that the first type head movement is head shaking, and the first reference waveform is a reference waveform corresponding to the head shaking. Taking FIG. 2 for example, it can be seen that the target waveform comprises two first reference waveforms, so that it can be determined that the user shakes the head twice. Similarity, the myoelectricity information shown in FIG. 3 indicates that the user nods twice.

In another example embodiment, the step S142 may comprise:

S1421b: determine a target signal characteristic in the myoelectricity information; and S1422b: determine the number of times of the first type head movement according to the number of first reference signal characteristics comprised in the target signal characteristic.

The implementation principle of the step S1411b is the same as that of the step S1411b, and no further details are provided herein again.

In the step S1422b, the target signal characteristic comprises the number of the first reference signal characteristics, which is corresponding to the number of times of the first type head movement. Still assume that the first type head movement is head shaking, and assume that the first reference signal characteristic is amplitude changing data (for example, the amplitude is increased to greater than 2 mV first and then decreased to smaller than −2 mV) corresponding to the head shaking. Taking FIG. 2 for example, it can be seen that the target signal characteristic in the myoelectricity information comprises two first reference signal characteristics, so that it can be determined that the user shakes the head twice. Certainly, a person skilled in the art understands that in the step, the waveform curve shown in FIG. 2 does not have to be obtained. Similarity, the myoelectricity information shown in FIG. 3 indicates that the user nods twice.

In addition, the head movement may further comprise head movements of other types, for example, a second type head movement, or the head movement may comprise head movements of multiple types simultaneously, for example, the head movement may comprise the first type head movement and the second type head movement simultaneously, and identification of the number of times of the head movements of various types may be implemented according to the foregoing implementation principle.

Figure 4:
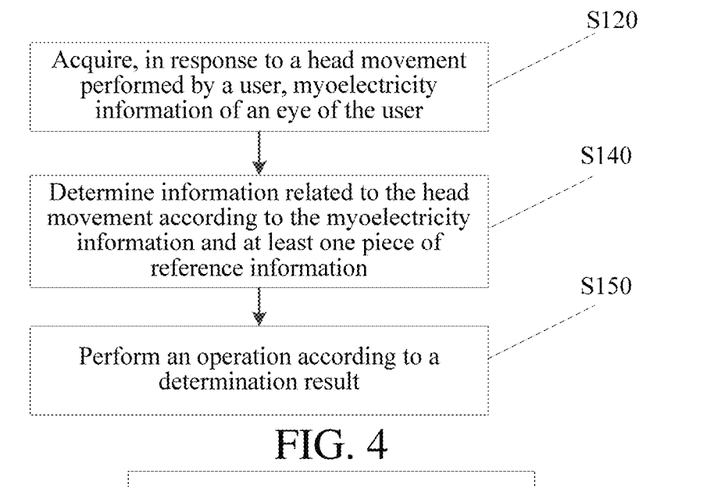
FIG. 4 is a flowchart of a method for determining a head movement according to an example embodiment of the present application.

Referring to FIG. 4, in an example embodiment, the method may further comprise:

S150: perform an operation according to a determination result.

The performed operation may comprise operations such as mode switching, content entering, user reminding, and device matching.

For example, during a process in which a user wears a pair of glasses, head movements of the user may be monitored, and if the user nods once, the current object is selected, for example, the current displayed application icon is selected; if the user nods twice continuously, the current object is open directly; and if the user shakes the head, a next object is switched to.

In addition, an embodiment of the present application further provides a computer readable medium, comprising computer readable instructions for performing the following operations when being executed: performing operations in the steps S120 and S140 in the method of the example embodiment shown in the foregoing FIG. 1.

In summary, in the method according to the embodiment of the present application, a head movement of a user may be determined according to eye myoelectricity information, and a corresponding operation is performed, and because an amplitude of the myoelectricity information is relatively high, accuracy of movement identification can be improved, and in some cases where a wearable device having the myoelectricity sensor, the user can easily control a corresponding electronic device by a head movement without adding implementation costs.

Figure 5:
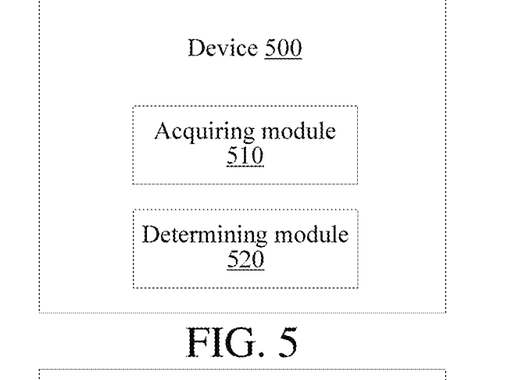
FIG. 5 is a module diagram of a device for determining a head movement according to another example embodiment of the present application.

FIG. 5 is a schematic module structural diagram of a device for determining a head movement according to an embodiment of the present application. The device may be an independent device for identifying a head movement, and certainly, the device may further be a functional module integrated in a wearable device such as a pair of glasses. Referring to FIG. 5, the device 500 may comprise:

an acquiring module 510, configured to acquire, in response to a head movement performed by a user, myoelectricity information of an eye of the user; and a determining module 520, configured to determine information related to the head movement according to the myoelectricity information and at least one piece of reference information.

In the device according to the embodiment of the present application, in response to a head movement performed by a user, myoelectricity information of an eye of the user is acquired; and according to the myoelectricity information and at least one piece of reference information, information related to the head movement is determined. Therefore, a device for identifying a head movement according to myoelectricity information is provided, which helps improve accuracy of head movement identification.

The following describes functions of the acquiring module 510 and the determining module 520 in detail with reference to the example embodiments.

The acquiring module 510 is configured to acquire, in response to a head movement performed by a user, myoelectricity information of an eye of the user.

The head movement refers to a movement performed by the head of the user, for example, head nodding and head shaking. The myoelectricity information may be myoelectricity information of the left eye or myoelectricity information of the right eye of the user, and for example, the acquiring module 510 may acquire the myoelectricity information of the eye by using a myoelectricity sensor.

The determining module 520 is configured to determine information related to the head movement according to the myoelectricity information and at least one piece of reference information.

Figure 6:
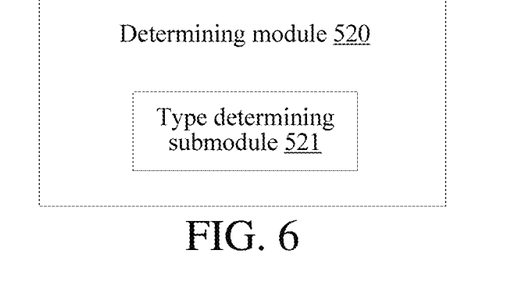
FIG. 6 is a module diagram of a determining module according to an example embodiment of the present application.

The information related to the head movement may comprise type of the head movement, for example, head nodding and head shaking. In an example embodiment, referring to FIG. 6, the determining module 520 comprises:

a type determining submodule 521, configured to determine the type of the head movement according to the myoelectricity information and the at least one piece of reference information.

Figure 7:
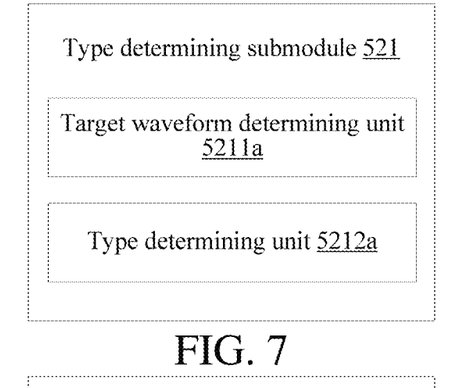
FIG. 7 is a module diagram of a type determining submodule according to an example embodiment of the present application.

In an example embodiment, referring to FIG. 7, the type determining submodule 521 may comprise:

a target waveform determining unit 5211a, configured to determine a target waveform in the myoelectricity information; and a type determining unit 5212a, configured to determine the type of the head movement according to the target waveform and at least one reference waveform.

In the target waveform determining unit 5211a, the target waveform is a waveform corresponding to the head movement in waveforms of the myoelectricity information, which is significantly different from waveforms of myoelectricity information collected when the head does not perform any movement.

Using an example in which the type of the head movement is head shaking movement for example, the obtained waveforms of the myoelectricity information are shown in FIG. 2. Waveforms in ellipses are waveforms when the head of the user performs the head shaking movement, and waveforms outside the ellipses are waveforms when the head of the user does not perform any movement. It can be seen that in FIG. 2, the waveforms in the ellipses are significantly different from the waveforms outside the ellipses. Specifically, amplitudes of the waveforms in the ellipses are obviously larger than amplitudes of the waveforms outside the ellipses. Based on this, the target waveforms can be extracted from the myoelectricity information, that is, the waveforms in the ellipses are determined as the target waveforms.

Similarity, FIG. 3 shows waveforms of the myoelectricity information obtained when the type of the head movement is head nodding. Waveforms in ellipses are waveforms when the head of the user performs the head nodding movement, and waveforms outside the ellipses are waveforms when the head of the user does not perform any movement. It can be seen that in FIG. 3, amplitudes of the waveforms in the ellipses are also obviously larger than amplitudes of the waveforms outside the ellipses. Based on this, it can be determined that the waveforms in the ellipses are the target waveforms.

In the type determining unit 5212a, the reference waveform may be a waveform that corresponds to a corresponding head movement obtained through pre-training, for example, during the training phase, the user may be trained to perform head movements of different types and the corresponding waveforms are correspondingly acquired as the reference waveforms. For example, during the training phase, the user is trained to perform a head shaking movement, and a waveform in the ellipse in FIG. 2 is correspondingly acquired as a reference waveform corresponding to the head shaking movement.

When the number of the at least one reference waveform is relatively smaller, that is, when there are relatively fewer types of the head movements, whether the target waveform comprises the at least one reference waveform can be determined in an image recognition manner, and if yes, it is determined that the type of the head movement is a type corresponding to the comprised reference waveform. Taking FIG. 2 and FIG. 3 for example, it can be seen that the target waveforms in FIG. 2 are significantly different from the target waveforms in FIG. 3. For example, the trend of the target waveforms in FIG. 2 is first ascending and then descending, and the trend of the target waveforms in FIG. 3 is first descending and then ascending. Based on the foregoing difference, it can be determined that the target waveforms correspond to different reference waveforms, that is, the target waveforms are identified.

When the number of the at least one reference waveform is relatively large, a probability of confusing different reference waveforms is increasing. In order to avoid an identification error, in an example embodiment, the type determining unit 5212a is configured to calculate cross correlations between the target waveform and the at least one reference waveform respectively, and determine the type of the head movement according to a calculation result.

Specifically, the type determining unit 5212a may calculate cross correlations between the target waveform and the at least one reference waveform respectively to obtain calculation results corresponding to each reference waveform, and then may select the type corresponding to the reference waveform whose value of the calculation result is the highest (that is, reference waveform that has the highest degree of correlation with the target waveform) as the type of the head movement. For example, assume that the at least one reference waveform comprises a first reference waveform corresponding to head nodding and a second reference waveform corresponding to head shaking, a cross correlation between the first reference waveform and the target waveform is calculated to obtain a first result, and a cross correlation between the second reference waveform and the target waveform is calculated to obtain a second result, and if the value of the first result is higher than the value of the second result, it can be determined that the type of the head movement is head nodding.

Figure 8:
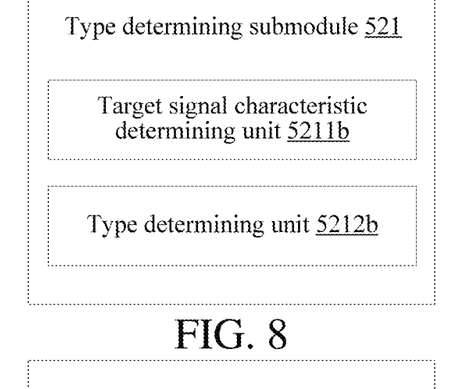
FIG. 8 is a module diagram of a type determining submodule according to another example embodiment of the present application.

In another example embodiment, referring to FIG. 8, the type determining submodule 521 may comprise:

a target signal characteristic determining unit 5211b, configured to determine a target signal characteristic in the myoelectricity information; and a type determining unit 5212b, configured to determine the type of the head movement according to the target signal characteristic and at least one reference signal characteristic.

In the target signal characteristic determining unit 5211b, the target signal characteristic may be understood as a signal characteristic of the target waveform in the foregoing example embodiment, which is correlated with at least one of an amplitude, a phase, and a spectrum of the target waveform. Specifically, the target signal characteristic may comprise at least one of a fingerprint, an average value, and a difference; the fingerprint may be composed of at least one of the amplitude, phase, and spectrum of the target waveform; the average value may be an average value of at least one of the amplitude, phase, and spectrum of the target waveform; and the difference may be a difference of at least one of the amplitude, phase, and spectrum of the target waveform. Certainly, a person skilled in the art understands that, the target signal characteristic may be directly determined according to data of the myoelectricity information, and does not have to be determined according to the target waveform.

In the type determining unit 5212b, the reference signal characteristic may be a signal characteristic that corresponds to a corresponding head movement obtained through pre-training, for example, during the training phase, the user may be trained to perform head movements of different types and the signal characteristics of the corresponding myoelectricity information are correspondingly acquired as the reference signal characteristics. For example, during the training phase, the user is trained to perform a head shaking movement, and a signal characteristic of the waveform in the ellipse in FIG. 2 is correspondingly acquired as a reference signal characteristic corresponding to the head shaking movement.

In the type determining unit 5212b, whether the target signal characteristic comprises the at least one reference signal characteristic can be determined in a signal characteristic comparison manner, and if yes, it is determined that the type of the head movement is a type corresponding to the comprised reference signal characteristic.

Figure 9:
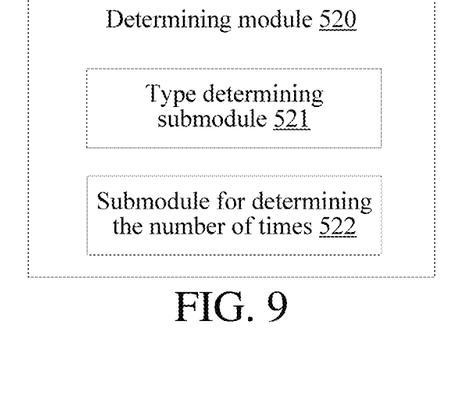
FIG. 9 is a module diagram of a determining module according to another example embodiment of the present application.

The type of the head movement may indicate different operating commands, for example, head nodding indicates confirmation and head shaking indicates cancellation. Meanwhile, for head movements of different types, different numbers of execution times may also indicate different operating commands, for example, a single head nodding indicates selected and two continuous head noddings indicate open. Therefore, in an example embodiment, the head movement comprises a first type head movement; and the at least one piece of reference information comprises first reference information corresponding to the first type head movement. Correspondingly, referring to FIG. 9, in another example embodiment, the determining module 520 further comprises:

a submodule for determining the number of times 522, configured to determine the number of times of the first type head movement according to the myoelectricity information and the first reference information.

Figure 10:
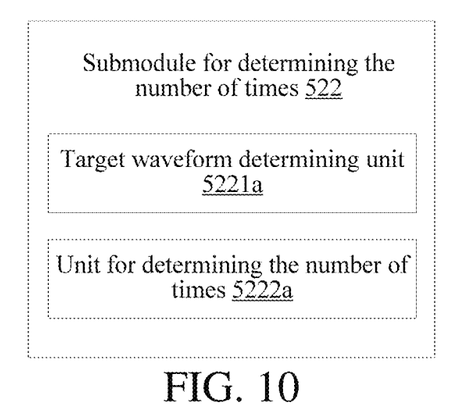
FIG. 10 is a module diagram of a submodule for determining the number of times according to an example embodiment of the present application.

In an example embodiment, referring to FIG. 10, the submodule for determining the number of times 522 may comprise:

a target waveform determining unit 5221a, configured to determine a target waveform in the myoelectricity information; and a unit for determining the number of times 5222a, configured to determine the number of times of the first type head movement according to the number of first reference waveforms comprised in the target waveform.

The implementation principle of the target waveform determining unit 5221a is the same as the implementation principle of the target waveform determining unit 5211a in the foregoing example embodiment, and no further details are provided herein again.

In the unit for determining the number of times 5222a, the number of the first reference waveforms comprised in the target waveform is corresponding to the number of times of the first type head movement. Assume that the first type head movement is head shaking, and the first reference waveform is a reference waveform corresponding to the head shaking. Taking FIG. 2 for example, it can be seen that the target waveform comprises two first reference waveforms, so that it can be determined that the user shakes the head twice. Similarity, the myoelectricity information shown in FIG. 3 indicates that the user nods twice.

Figure 11:
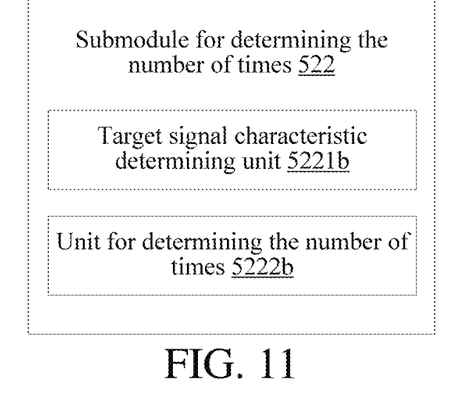
FIG. 11 is a module diagram of a submodule for determining the number of times according to another example embodiment of the present application.

In another example embodiment, referring to FIG. 11, the submodule for determining the number of times 522 comprises:

a target signal characteristic determining unit 5221b, configured to determine a target signal characteristic in the myoelectricity information; and a unit for determining the number of times 5222b, configured to determine the number of times of the first type head movement according to the number of first reference signal characteristics comprised in the target signal characteristic.

The implementation principle of the target signal characteristic determining unit 5221b is the same as the implementation principle of the target signal characteristic determining unit 5211b in the foregoing example embodiment, and no further details are provided herein again.

In the unit for determining the number of times 5222b, the target signal characteristic comprises the number of the first reference signal characteristics, which is corresponding to the number of times of the first type head movement. Still assume that the first type head movement is head shaking, and assume that the first reference signal characteristic is amplitude changing data (for example, the amplitude is increased to greater than 2 mV first and then decreased to smaller than −2 mV) corresponding to the head shaking. Taking FIG. 2 for example, it can be seen that the target signal characteristic in the myoelectricity information comprises two first reference signal characteristics, so that it can be determined that the user shakes the head twice. Certainly, a person skilled in the art understands that in the step, the waveform curve shown in FIG. 2 does not have to be obtained. Similarity, the myoelectricity information shown in FIG. 3 indicates that the user nods twice.

In addition, the head movement may further comprise head movements of other types, for example, a second type head movement, or the head movement may comprise head movements of multiple types simultaneously, for example, the head movement may comprise the first type head movement and the second type head movement simultaneously, and identification of the number of times of the head movements of various types may be implemented according to the foregoing implementation principle.

Figure 12:
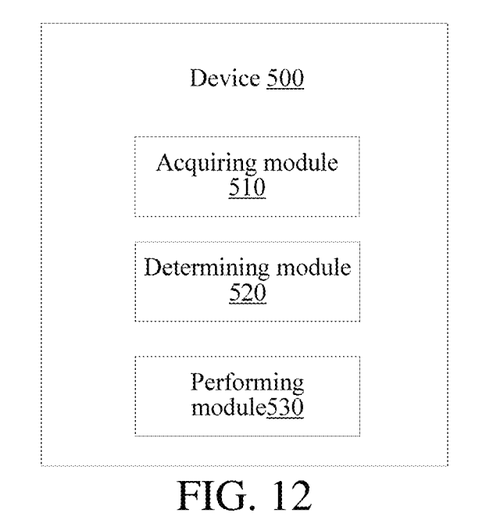
FIG. 12 is a module diagram of a device for determining a head movement according to another example embodiment of the present application.

Referring to FIG. 12, in an example embodiment, the device 500 further comprises:

a performing module 530, configured to perform an operation according to a determination result.

The performed operation may comprise operations such as mode switching, content entering, user reminding, and device matching.

In summary, in the device according to the embodiment of the present application, a head movement of a user may be determined according to eye myoelectricity information, and a corresponding operation is performed, which helps improve accuracy of movement identification, and in some cases where a wearable device having a corresponding sensor, the user can easily control a corresponding electronic device by a head movement without adding implementation costs.

An application scenario of the method and device for determining a head movement of the embodiments of the present application may as follows: a user wears a pair of glasses, and the pair of glasses initially enters a first level menu, a myoelectricity sensor thereon acquires an eye myoelectricity signal of the user; the user performs a head shaking movement, and the pair of glasses identifies the head shaking movement, and therefore controls items of the first level menu to switch in a display window of the pair of glasses according to a predefined sequence; and when an application a user wants to open is switched to, the user performs a head nodding movement, the application is selected, and then the user nods twice continuously, the application is open.

Figure 13:
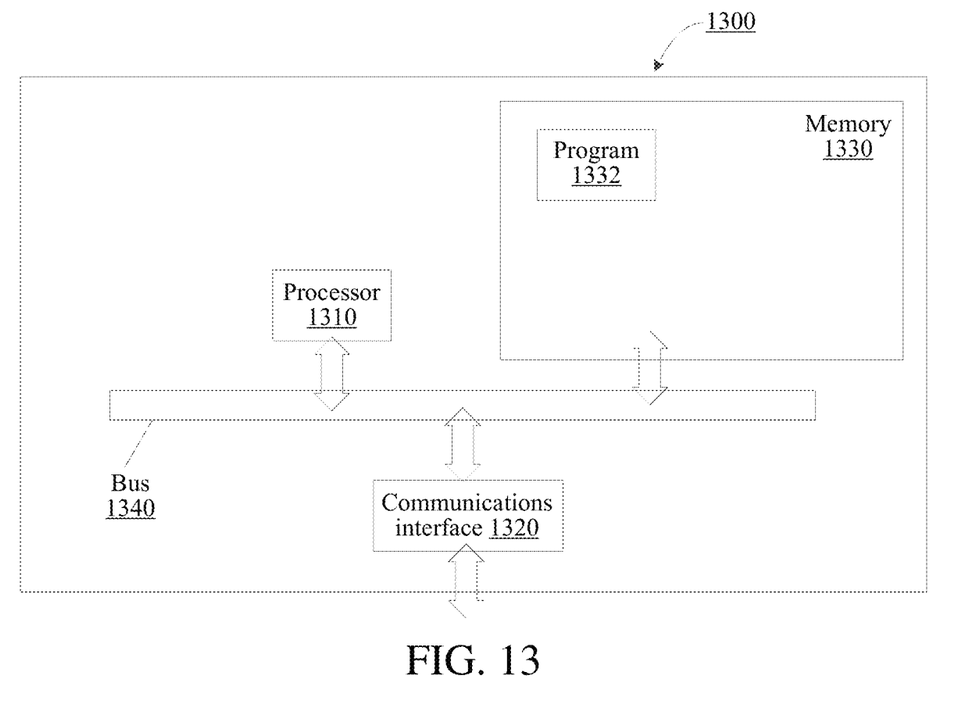
FIG. 13 is a schematic hardware structural diagram of a device for determining a head movement according to an example embodiment of the present application.

A hardware structure of a device for determining a head movement according to another example embodiment of the present application is shown in FIG. 13. Specific embodiments of the present application are not intended to limit specific implementations of the device for determining a head movement. As shown in FIG. 13, the device 1300 may comprise:

a processor 1310, a communications interface 1320, a memory 1330, and a communications bus 1340.

The processor 1310, the communications interface 1320, and the memory 1330 communicate with each other by using the communications bus 1340.

The communications interface 1320 is configured to communicate with other network elements.

The processor 1310 is configured to execute a program 1332. Specifically, the processor 1310 may perform relevant steps in the foregoing method embodiment shown in FIG. 1.

Specifically, the program 1332 may comprise program code, wherein the program code comprises a computer operation instruction.

The processor 1310 may be a central processing unit (CPU), an application specific integrated circuit (ASIC), or one or more integrated circuits configured to implement the embodiments of the present application.

The memory 1330 is configured to store the program 1332. The memory 1330 may comprise a high-speed RAM memory, or may further comprise a non-volatile memory, for example, at least one magnetic disk storage. The program 1332 may be specifically used to perform the following steps:

acquire, in response to a head movement performed by a user, myoelectricity information of an eye of the user; and determine information related to the head movement according to the myoelectricity information and at least one piece of reference information.

For specific implementations of the steps in the program 1332, reference may be made to the corresponding steps or modules in the foregoing embodiments, and no further details are provided herein again. It may be clearly understood by a person skilled in the art that, for the purpose of convenient and brief description, for detailed working procedures of the foregoing devices and modules, reference may be made to the description of corresponding procedures in the foregoing method embodiments, and no further details are provided herein again.

A person of ordinary skill in the art may be aware that, in combination with the examples described in the embodiments disclosed in this specification, units and method steps may be implemented by means of electronic hardware or a combination of computer software and electronic hardware. Whether these functions are executed as hardware or software depends upon the particular application and design constraint conditions of the technical solutions. A person skilled in the art may use different methods to implement the described functions for each particular application, but it should not be considered that the implementation goes beyond the scope of the present application.

When the functions are implemented in a form of a software functional unit and sold or used as an independent product, the functions may be stored in a computer-readable storage medium. Based on such an understanding, the technical solutions of the present application essentially, or the part contributing to the prior art, or some of the technical solutions may be implemented in a form of a software product. The computer software product is stored in a storage medium, and comprises several instructions for instructing a computer device (which may be a personal computer, a server, a network device, or the like) to perform all or some of the steps of the methods in the embodiments of the present application. The foregoing storage medium comprises: any medium that can store program code, such as a USB flash drive, a removable hard disk, a read-only memory (ROM), a random access memory (RAM), a magnetic disk, or an optical disc.

The above example embodiments are only used to describe the present application, rather than limit the present application; various alterations and variants can be made by a person of ordinary skill in the art without departing from the spirit and scope of the present application, so all equivalent technical solutions also belong to the scope of the present application, and the scope of patent protection of the present application should be defined by claims.

What is claimed is:

1. A method, comprising:
acquiring, by a system comprising a processor, in response to a head movement performed by a user, myoelectricity information of an eye of the user; and
determining, by the system, information related to the head movement according to the myoelectricity information and at least one piece of reference information, wherein the determining the information related to the head movement according to the myoelectricity information and the at least one piece of reference information comprises:
determining a type of the head movement according to the myoelectricity information and the at least one piece of reference information, and
determining a number of times of the type of the head movement according to the myoelectricity information and the at least one piece of reference information.

2. The method of claim 1, wherein the type of the head movement comprises:
at least one of a head nodding type or a head shaking type.

3. The method of claim 1, wherein the determining the type of the head movement according to the myoelectricity information and the at least one piece of reference information comprises:
determining a target waveform in the myoelectricity information; and
determining the type of the head movement according to the target waveform and at least one reference waveform.

4. The method of claim 3, wherein the determining the type of the head movement according to the target waveform and the at least one reference waveform comprises:
calculating cross correlations between the target waveform and the at least one reference waveform respectively; and
determining the type of the head movement according to a result of the calculating.

5. The method of claim 1, wherein the determining the type of the head movement according to the myoelectricity information and the at least one piece of reference information comprises:
determining a target signal characteristic in the myoelectricity information; and
determining the type of the head movement according to the target signal characteristic and at least one reference signal characteristic.

6. The method of claim 1, wherein the determining the number of times of the type of the head movement according to the myoelectricity information and the at least one piece of reference information comprises:
determining a target waveform in the myoelectricity information; and determining the number of times of the type of the head movement according to a number of reference waveforms comprised in the target waveform.

7. The method of claim 1, wherein the determining the number of times of the type of the head movement according to the myoelectricity information and the at least one piece of reference information comprises:
   determining a target signal characteristic in the myoelectricity information; and
   determining the number of times of the type of the head movement according to a number of reference signal characteristics comprised in the target signal characteristic.

8. The method of claim 1, further comprising:
   performing, by the system, an operation according to a result of the determining the information.

9. A device, comprising:
   at least one sensor;
   a memory that stores executable modules; and
   a processor, coupled to the memory, that executes or facilitates execution of the executable modules, the executable modules comprising:
      an acquiring module configured to acquire, by the at least one sensor, in response to a head movement determined to have been performed by a user, myoelectricity information of an eye of the user; and
      a determining module configured to determine movement information related to the head movement according to the myoelectricity information and a piece of reference information, wherein the myoelectricity information comprises a myoelectricity waveform, and wherein the determining module comprises:
         a type determining submodule configured to determine a type of the head movement according to the myoelectricity information and the piece of reference information, wherein a first amplitude of the myoelectricity waveform determines the type of head movement, and
         a number determination submodule configured to determine a number of times of the type of the head movement according to the myoelectricity information and the piece of reference information, wherein a number of times the first amplitude occurs determines the number of times of the type of head movement.

10. The device of claim 9, wherein the type determining submodule comprises:
    a target waveform determining unit configured to determine a target waveform in the myoelectricity information, wherein the target waveform comprises a myoelectricity waveform with a second amplitude corresponding to the head movement; and
    a type determining unit configured to determine the type of the head movement according to the target waveform and at least one reference waveform, wherein the at least one reference waveform comprises a myoelectricity waveform with a third amplitude corresponding to a predetermined head movement.

11. The device of claim 10, wherein the type determining unit is configured to:
    cross correlate the target waveform and the at least one reference waveform to yield a cross correlation result, wherein the cross correlation of the target waveform and the at least one reference waveform comprises:
       selecting a reference waveform of the at least one reference waveform that has a highest correlation with the target waveform; and
    determine the type of the head movement according to the cross correlation result.

12. The device of claim 9, wherein the type determining submodule comprises:
    a target signal characteristic determining unit configured to determine a target signal characteristic in the myoelectricity information, wherein the target signal characteristic comprises at least one of:
       a fingerprint comprising at least one of an amplitude of the target waveform, a phase of the target waveform, or a spectrum of the target waveform,
       an average value of at least one of an amplitude of the target waveform, a phase of the target waveform, or a spectrum of the target waveform, or
       a difference of at least one of an amplitude of the target waveform, a phase of the target waveform, or a spectrum of the target waveform; and
    a type determining unit configured to determine the type of the head movement according to the target signal characteristic and a reference signal characteristic, wherein the target signal characteristic and the reference signal characteristic are compared.

13. The device of claim 9, wherein the number determination submodule comprises:
    a target waveform determining unit configured to determine a target waveform in the myoelectricity information, wherein the target waveform comprises a myoelectricity waveform with a fourth amplitude corresponding to the head movement; and
    a number determination unit configured to determine the number of times of the type of the head movement according to the number of reference waveforms comprised in the target waveform, wherein the number of reference waveforms corresponds to the number of times of the type of head movement.

14. The device of claim 9, wherein the number determination submodule comprises:
    a target signal characteristic determining unit configured to determine a target signal characteristic in the myoelectricity information, wherein the target signal characteristic comprises at least one of:
       a fingerprint comprising at least one of an amplitude of the target waveform, a phase of the target waveform, or a spectrum of the target waveform,
       an average value of at least one of an amplitude of the target waveform, a phase of the target waveform, or a spectrum of the target waveform, or
       a difference of at least one of an amplitude of the target waveform, a phase of the target waveform, or a spectrum of the target waveform; and
    a number determination unit configured to determine the number of times of the type of the head movement according to a number of reference signal characteristics comprised in the target signal characteristic, wherein the number of reference signal characteristics corresponds to the number of times of the type of head movement.

15. The device of claim 9, wherein the executable modules further comprise:
    a performing module configured to perform an operation according to a determination result of the movement information being determined, wherein the operations comprise at least one of mode switching, content entering, user reminding, or device matching.

16. The device of claim 9, wherein the device is included in a wearable device.

17. A non-transitory computer-readable storage device, comprising:
a memory that stores at least one executable instruction; and
a processor that executes or facilitates the at least one executable instruction, to perform operations, comprising:
acquiring, in response to a head movement performed by a user, myoelectricity information of an eye of the user; and
determining information related to the head movement according to the myoelectricity information and at least one piece of reference information,
wherein the determining information related to the head movement according to the myoelectricity information and at least one piece of reference information comprises:
determining a type of the head movement according to the myoelectricity information and the at least one piece of reference information, and
determining a number of times of the type of the head movement according to the myoelectricity information and the at least one piece of reference information.

18. The non-transitory computer-readable storage device of claim 17, wherein the type of the head movement comprises:
at least one of a head nodding type or a head shaking type.

19. The non-transitory computer-readable storage device of claim 17, wherein the determining the type of the head movement according to the myoelectricity information and the at least one piece of reference information comprises:
determining a target waveform in the myoelectricity information; and
determining the type of the head movement according to the target waveform and at least one reference waveform.

20. A device comprising:
a processor;
a memory; and
a communications bus, wherein the memory stores executable instructions, the processor is connected to the memory through the communication bus, and when the device operates, the processor executes the executable instructions stored in the memory, so that the device performs operations, comprising:
in response to determining that a head movement associated with a user identity has been performed, acquiring, myoelectricity information of an eye determined to be associated with the user identity; and
determining head movement information related to the head movement according to the myoelectricity information and reference information,
wherein the determining the head movement information related to the head movement according to the myoelectricity information and reference information comprises:
determining a type of the head movement according to the myoelectricity information and the reference information, and
determining a number of times of the type of the head movement according to the myoelectricity information and the reference information.

21. The device of claim 20, wherein, the type of the head movement comprises:
at least one of a head nodding type or a head shaking type.

22. The device of claim 20, wherein the determining the type of the head movement according to the myoelectricity information and the at least one piece of reference information comprises:
determining a target waveform in the myoelectricity information; and
determining the type of the head movement according to the target waveform and at least one reference waveform.

* * * * *